United States Patent
Wofford et al.

(10) Patent No.: US 6,335,961 B1
(45) Date of Patent: Jan. 1, 2002

(54) INTEGRATED HIGH DEFINITION INTENSITY MULTILEAF COLLIMATOR SYSTEM WHICH PROVIDES IMPROVED CONFORMAL RADIATION THERAPY WHILE MINIMIZING LEAKAGE

(75) Inventors: Mark Wofford, Martinez; Francisco M. Hernandez-Guerra, Concord; Joseph S. Saba, Walnut Creek; Todd H. Steinberg, Antioch, all of CA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/234,362

(22) Filed: Jan. 20, 1999

Related U.S. Application Data (60) Provisional application No. 60/103,454, filed on Oct. 6, 1998.

(51) Int. Cl.$^7$ .................................................. A61N 5/10
(52) U.S. Cl. ........................................ 378/65; 378/151
(58) Field of Search ........................... 378/65, 150, 151

(56) References Cited

U.S. PATENT DOCUMENTS

| | | | | |
|---|---|---|---|---|
| 5,663,999 A | * | 9/1997 | Siochi ........................ | 378/65 |
| 5,771,270 A | * | 6/1998 | Archer ....................... | 378/65 |
| 5,818,902 A | | 10/1998 | Yu | |
| 6,049,587 A | * | 4/2000 | Leksell et al. ............... | 378/65 |

FOREIGN PATENT DOCUMENTS

| JP | 07 0255718 | 10/1995 |
|---|---|---|
| JP | 08 0131566 | 5/1996 |

OTHER PUBLICATIONS

Welch, M.E., "Precision small field dosimetry using a Philips Multileaf Collimator",*17th International Cancer Congress*, Rio de Janeiro, Brazil, Aug. 1998, pp. 1655–1659.

Welch, M.E., "Quality assurance regimes for Multileaf Collimators", *17th International Cancer Congress*, Rio de Janeiro, Brazil, Aug. 1998, pp. 1649–1653.

Welch, M.E., "Clinical experience of conformal therapy using a Philips Multileaf Collimator", *5th International Meeting on Progress in Radio–Oncology*, ICRO/OGRO 5, Salzburg, Austria, May 1995, pp. 359–361.

Welch, M., "Quality assurance regimes to ensure a multileaf collimator (MLC) performance for precision small field dosimetry. Do MLC's shape up?", *6th International Meeting on Progress in Radio–Oncology*, ICRO/OGRO 6, Salzburg, Austria, May 1998, pp. 627–631.

* cited by examiner

*Primary Examiner*—Craig E. Church (57) ABSTRACT

A method and system in accordance with the present invention uses the existing hardware and divides the treatment port dose into segments. In between each segment the field, with respect to the beam, would be translated, and the leaf positions would be adjusted to maintain the tumor contour. By integrating the above-identified methodology with a hardware system, accurate conformal radiation therapy is provided while minimizing leakage. In addition, through the present invention, higher dose rates can be provided while not appreciably affecting treatment time.

15 Claims, 8 Drawing Sheets

$\theta = 0 \cdot \deg, 10 \cdot \deg \ldots 360 \cdot \deg$  Collimator Angle  $\beta := 330 \cdot \deg$  Table Isocentric Angle $\alpha = 0 \cdot \deg, 10 \cdot \deg \ldots 360 \cdot \deg$  Gantry Angle  $\gamma := 60 \cdot \deg$  Table Column (Eccentric) Angle $S = 1$   Step Size  $\phi := \beta + \gamma$   $\phi = 390 \cdot \deg$   Table Total Angle $x(\theta, \alpha) := -S \cdot \sin(\theta) \cdot \cos(\alpha)$   Global Lateral Shift $y(\theta) := S \cdot \cos(\theta)$   Global Longitudinal Shift $z(\theta, \alpha) := -S \cdot \sin(\theta) \cdot -\sin(\alpha)$   Global Vertical Shift = Table Vertical Shift $S_{xy}(\theta, \alpha) = \sqrt{x(\theta, \alpha)^2 + y(\theta)^2}$   Step size projected to global xy plane Using the transformation of axes (*Calculus with Analytic Geometry*, Swokowski, p282):

$x_{table}(\theta, \alpha) = x(\theta, \alpha) \cdot \cos(\phi) + y(\theta) \cdot \sin(\phi)$   Table lateral shift $y_{table}(\theta, \alpha) = -x(\theta, \alpha) \cdot \sin(\phi) + y(\theta) \cdot \cos(\phi)$   Table longitudinal shift

INTEGRATED HIGH DEFINITION INTENSITY MULTILEAF COLLIMATOR SYSTEM WHICH PROVIDES IMPROVED CONFORMAL RADIATION THERAPY WHILE MINIMIZING LEAKAGE

This application is a Continuation-in-Part application of provisional patent application serial No. 60/103,454 filed Oct. 6, 1998, which is incorporated by reference in its entirety herewith.

FIELD OF THE INVENTION

The present invention relates to collimators in radiation therapy devices, and more particularly to a technique for providing a high resolution multileaf collimator treatment delivery.

BACKGROUND OF THE INVENTION

During conventional radiation therapy treatment, a beam of radiation, varying in angles and intensities, is directed at an area of a patient, e.g., at a tumor. Typical treatment field shapes, square, rectangular, or a modification thereof, result in a three-dimensional treatment volume that, unfortunately, may include healthy tissue and organs. For obvious safety reasons, the dose capable of being delivered to the tumor is limited by the healthy tissue and organs in the path of the radiation beam. Since cure rates for many tumors are a sensitive function of the dose they receive, reducing the amount of exposed healthy tissue and organs is highly desirable in order to be able to increase the dose delivered to the tumor. Methods of making the treatment volume correspond more closely with a tumor include moving solid-jaw blocks during treatment, scanning the radiation beam over the volume to be treated, and using a multileaf collimator to create an irregularly shaped field related to the shape of the tumor.

An example of a multileaf collimator arrangement positioned about the central axis of a radiation-emitting head for shaping an irradiated beam is disclosed in U.S. Pat. No. 5,166,531, issued to Hunzinger on Nov. 24, 1992. Two opposing arrays of side-by-side elongated radiation blocking collimator leaves act in place of opposing solid jaw blocks. Each leaf in each opposing array can be moved longitudinally towards or away from the central axis of the beam, thus defining a desired shape through which the radiation beam will pass.

An enhancement on the multileaf collimator approach is described in U.S. Pat. No. 5,591,983, issued to Yao on Jan. 7, 1997. In Yao, a multiple layer multileaf collimator design is formed through first and second layers of a plurality of elongated radiation blocking leaves. The leaves of each layer are arranged adjacent one another so as to form two opposed rows of adjacently positioned leaves and are movable in a longitudinal direction which can be either generally transverse to or in the same direction of the beam. The layers are arranged one above another in the beam direction and offset in a lateral direction, so that spaces between adjacent leaves of the first and second layers are positioned over and under, respectively, leaves of the respective first and second layers. The arrangement of the leaves allows a reduction in problems of radiation leakage between leaves of a multileaf collimator. However, the arrangement does not provide as fine a resolution as desired to allow more accurate block positioning for creating a block volume in correspondence with a tumor shape.

Multileaf collimators are being used to replace lead alloy blocks in many conformal treatments today. However, there are still a number of treatment cases that require the use of blocks because conformal shaping could not be adequately accomplished using an MLC. This is so because of the so-called "stair-step" effect that occurs at field edges that are not perpendicular to the leaf face edges. An undulating dose pattern at the border of an irradiated volume results when the leaves are stepped to create an irregular shape. This distribution is unacceptable for field edges that are next to critical structures or when abutment of additional fields is planned.

There are solutions to address this problem of undulating dose patterns at a stepped MLC edge. First, blocks could continue to be used to define the shape. Second, the collimator could be rotated to bring the leaves in perpendicular to the field edge of interest. Finally, a Micro Multileaf Collimator could be utilized that has smaller leaves such as 0.5 cm widths.

Below are the advantages and disadvantages of each of these solutions.

1. Lead Alloy Blocks
Advantages:
Nicely defined edges around target and critical structures
Best penumbra results
Disadvantages:
All the same disadvantages as the block vs MLC argument
Block creating
Entering the room between each field
5% leakage
costly
2. Collimator Rotation
Advantages:
The collimator can be rotated to bring the leaves in perpendicular to the critical field edge
Disadvantages:
This technique is only viable if the MLC system is capable of rotating independently of any secondary jaw system, resulting in new mechanical complexity
This technique may move the undulating pattern to other positions along the field edge
3. Micro Multileaf Collimator
Advantages:
All the same advantages over a block solution
Better field edge definition than the original "stair-stepped" MLC shape
Disadvantages:
Most leakage of any solution
Increased number of leaves and motors can lead to serious mechanical and reliability issues
Design issues integrating it into the Collimator head
Can only handle smaller fields
Won't have doubly focused leaves—poor penumbra
Manufacturability issues
Very costly Accordingly, what is needed is a system and method for utilizing a multiple layer multileaf collimator arrangement that improves resolution and reduces leakage for radiation delivery. The present invention addresses such a need.

SUMMARY OF THE INVENTION

A method and system in accordance with the present invention uses the existing hardware and divides the treatment port dose into segments. In between each segment, the field, with respect to the beam, would be translated, and the leaf positions would be adjusted to maintain the tumor contour.

By integrating the above-identified methodology with a hardware system, accurate conformal radiation therapy is provided while minimizing leakage. In addition, through the present invention, higher dose rates can be provided while not appreciably affecting treatment time.

Accordingly, a system and method in accordance with the present invention provides for better defined edges around target and critical surfaces than a conventional multileaf collimator (i.e., effective penumbra). It provides for the same clearance as conventional MLC. It provides for the same maximum field size as a conventional MLC. Finally, a system and method in accordance with the present invention minimizes leakage between the leafs thereby minimizing leakage to the patient.

DETAILED DESCRIPTION OF THE INVENTION

Definitions

Automatic Sequencing: The process of automatically downloading a Group of fields or segments from the V&R to the control of the linear accelerator sequentially, without user intervention.

Control Console: The interface and controller of a linear accelerator. The control console interfaces to the V&R.

Dynamic leaf motion: leaf motion while beam is on

Effective penumbra: the effective penumbra for any combination of high and low isodose lines measures the distance between the points on the higher isodose that comes closest to the target and the points on the lower isodose that come closest to the critical structure.

EPID: Electronic Portal Imaging Device

Field Group: An arbitrary grouping mechanism used to relate several Fields together. This relationship is usually based on the desire to autosequence them the Fields together.

HDI: High definition intensity. Creating high-resolution MLC fields through the use of an MLC, software algorithms, and automatic table motion.

Intensity Map: A 3D representation of desired or delivered radiation intensity distribution from a particular port.

Intensity Modulation: The process of shaping, modifying, and moving the beam around a target in order to maximize the dose at the target and minimize the dose to all normal structures.

LANTIS: Local Area Network Therapy Information System

MLC: Multileaf Collimator

Monitor Units: the unit of measurement for delivery of radiation on a linear accelerator. Monitor units are related to dose by an algebraic formula using dose coefficients.

MU: monitor units

Port: used to describe the port of entry for an external beam treatment. A subset of the information contained in a field.

Port film: A film image acquired at the linear accelerator created from the exit dose radiation from the patient.

Portal imaging: Capturing an image from the radiation exiting from the patient either on film or as an electronic image.

Segment: a piece of a treatment field. Multiple segments are usually used to create an intensity modulated field or a complex dynamic field. Segments are sequenced together to create a field.

Static field: a treatment field or segment defined with no moving parameters such as leaves or gantry angles. Static segments can be built up to create an intensity modulated field.

Step and shoot: A method of intensity modulation of sequentially delivering static fields.

Treatment record: The record of what was delivered to the patient on the linear accelerator Includes all the machine settings and parameters.

V&R: Verify and Record, the interface to a linear accelerator for downloading fields, verifying the fields before delivery, and recording the delivered field parameters.

V&R software: Software utilized to control the position of the leaves in the multileaf collimator.

DESCRIPTION OF THE INVENTION

The present invention relates to modulation of radiation delivery to achieve finer resolution and control. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. In the following, the invention is described with primary reference to a system for delivering X-ray radiation to a field of a patient, and for delimiting the field using at least one movable leaf in the beam path from a radiation source. This is by way of example. Thus, the present invention is not intended to be limited to the embodiment shown but is to be accorded the widest scope consistent with the principles and features described herein.

Figure 1:
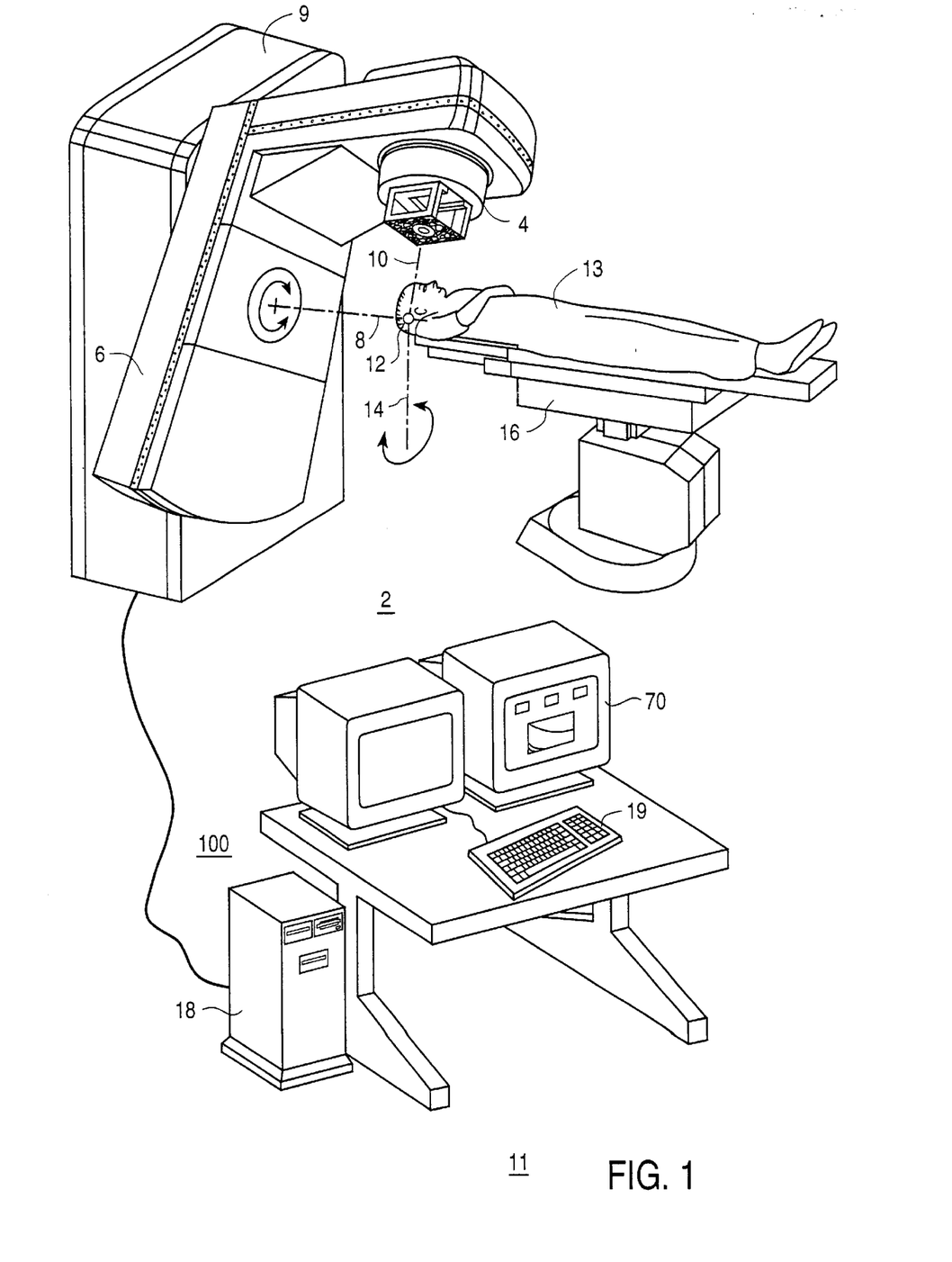
FIG. 1 illustrates a radiation treatment device.

FIG. 1 illustrates a radiation treatment device 2 of common design, which utilizes a multileaf collimator (MLC) 4 and a control unit in a housing 9 along with a treatment processing unit 100 constructed in accordance with the present invention. The radiation treatment device 2 comprises a gantry 6 which can be swiveled around a horizontal axis of rotation 8 in the course of therapeutic treatment. MLC 4 are fastened to a projection of gantry 6. To generate the high-powered radiation required for the therapy, a linear accelerator is located in gantry 6. The axis of the radiation bundle emitted from the linear accelerator and gantry 6 is designated 10. Electron, photon, or any other detectable radiation can be used for the therapy.

During the treatment, the radiation beam is trained on a zone 12 of an object 13, for example, a patient who is to be treated, and who lies at the isocenter of the gantry rotation. The rotational axis 8 of the gantry 6, the rotational axis 14 of a treatment table 16, and the beam axis 10 all preferably intersect in the isocenter. The construction of such a radiation treatment device is described in general in a brochure "Digital Systems for Radiation Oncology", Siemens Medical Laboratories, Inc. A91004-M2630-B358-01-4A00, September 1991.

Figure 2:
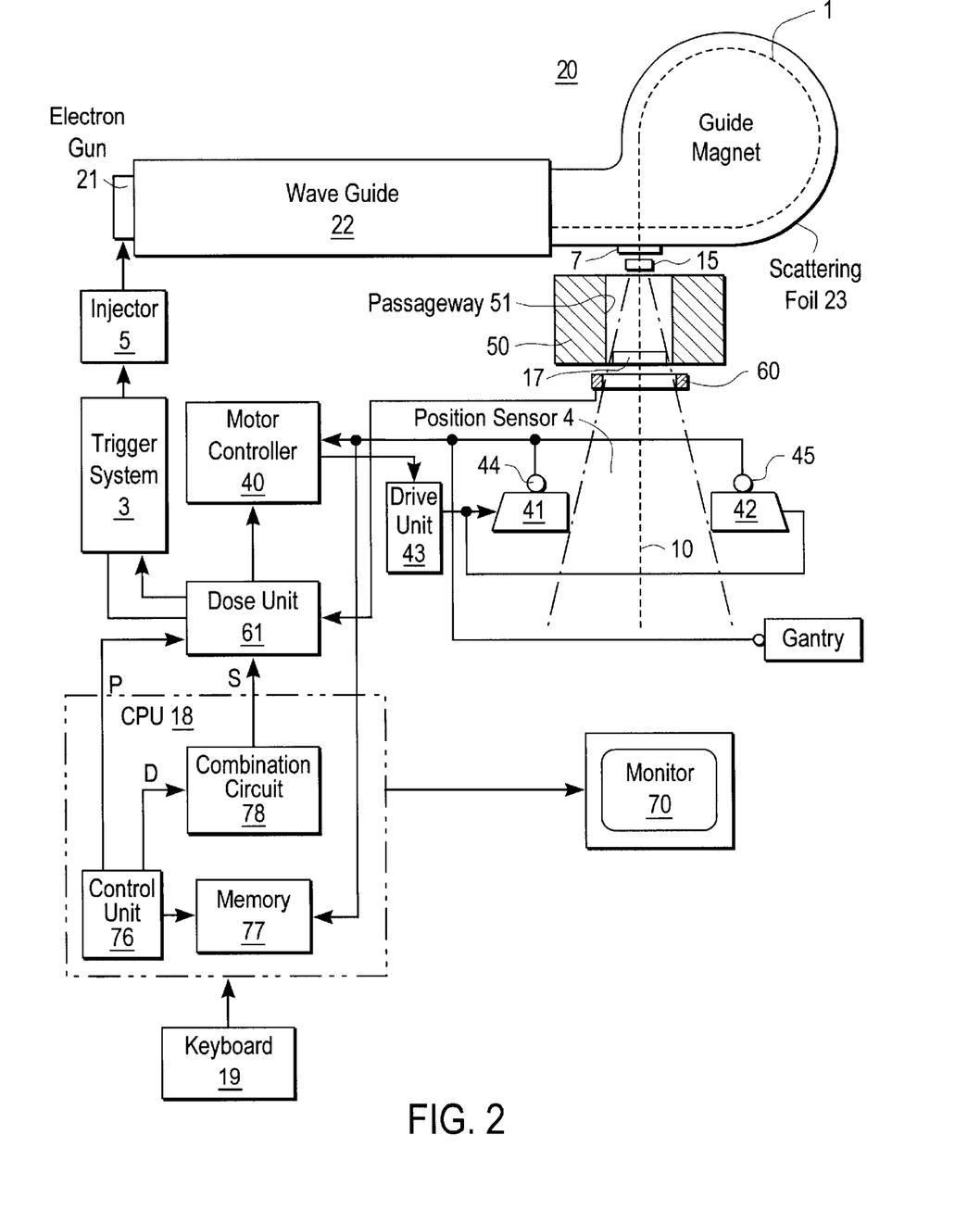
FIG. 2 shows a portion of an illustrative radiation treatment device.

FIG. 2 shows a portion of an illustrative radiation treatment device 2 and portions of treatment processing unit 100 in more detail. An electron beam 1 is generated in an electron accelerator 20. Accelerator 20 comprises an electron gun 21, a wave guide 22, and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a first scattering foil 15, the beam goes through a passageway 51 of a shield block 50 and encounters a second scattering foil 17. Next, the beam is sent through a measuring chamber 60, in which the dose is ascertained. If the scattering foils are replaced by a target, the radiation beam is an X-ray beam. Finally, MLC 4 includes a plurality of leaves 41 and 42. Of course, this is just one example of a beam-shielding arrangement that can be used in the invention. The invention is suitable in other arrangements, as is well appreciated by those skilled in the art.

The MLC 4 comprises a plurality of leaves 41 and 42 and an additional pair of aperture plates (not shown) arranged perpendicular to the plurality of leaves 41 and 42. In order to change the size of the irradiated field, the plurality of leaves can be moved with respect to axis 10 by a drive unit 43 which is indicated in FIG. 2 only with respect to leaf 41. Drive unit 43 comprises an electric motor which is coupled to leaves 41 and 42 and which is controlled by a motor controller 40. Position sensors 44 and 45 are also coupled to leaves 41 and 42, respectively, for sensing their positions.

The area of a patient that is irradiated is known as the field. As is well known, leaves 4 are substantially impervious to the emitted radiation. They are mounted between the radiation source and patient in order to delimit the field. Areas of the body, for example, healthy tissue, are therefore subjected to as little radiation as possible, and preferably to none at all. Preferably, with at least one of the leaves movable, the distribution of radiation over the field need not be uniform (one region can be given a higher dose than another); further, with the gantry able to be rotated, different beam angles and radiation distributions are allowed without having to move the patient around. The central treatment processing or control unit 100 (FIG. 1) is usually located apart from radiation treatment device 2 in a different room to protect the therapist from radiation. Treatment processing unit 100 includes an output device, such as at least one visual display unit or monitor 70, and an input device, such as a keyboard 19, although data can be input also through data carriers, such as data storage devices. The treatment processing unit 100 is typically operated by the therapist who administers actual delivery of a radiation treatment as prescribed by an oncologist. By utilizing keyboard 19, or other input device, the therapist enters into a control unit 76 of the treatment processing unit 100 the data that defines the radiation to be delivered to the patient, for example, according to the prescription of the oncologist. The program can also be input via another input device, such as a data storage device, through data transmission. On the screen of a monitor 70, various data can be displayed before and during the treatment.

Central processing unit 18, included in treatment processing unit 100, is connected with the input device, e.g., keyboard 19, for inputting the prescribed delivery of the radiation treatment and with a dose control unit 61 that generates the desired values of radiation for the controlling trigger system 3. Trigger system 3 suitably adapts the pulse repetition frequency or other parameters to change the radiation output. A digital dosimetry system is particularly advantageous in order to more easily control the digital output of central processing unit 18. Central processing unit 18 suitably includes a control unit 76 for controlling execution of the treatment program in conjunction with memory 77 and a combination circuit 78 which suitably receives signals from the control unit 76 and memory 77.

Figure 3:
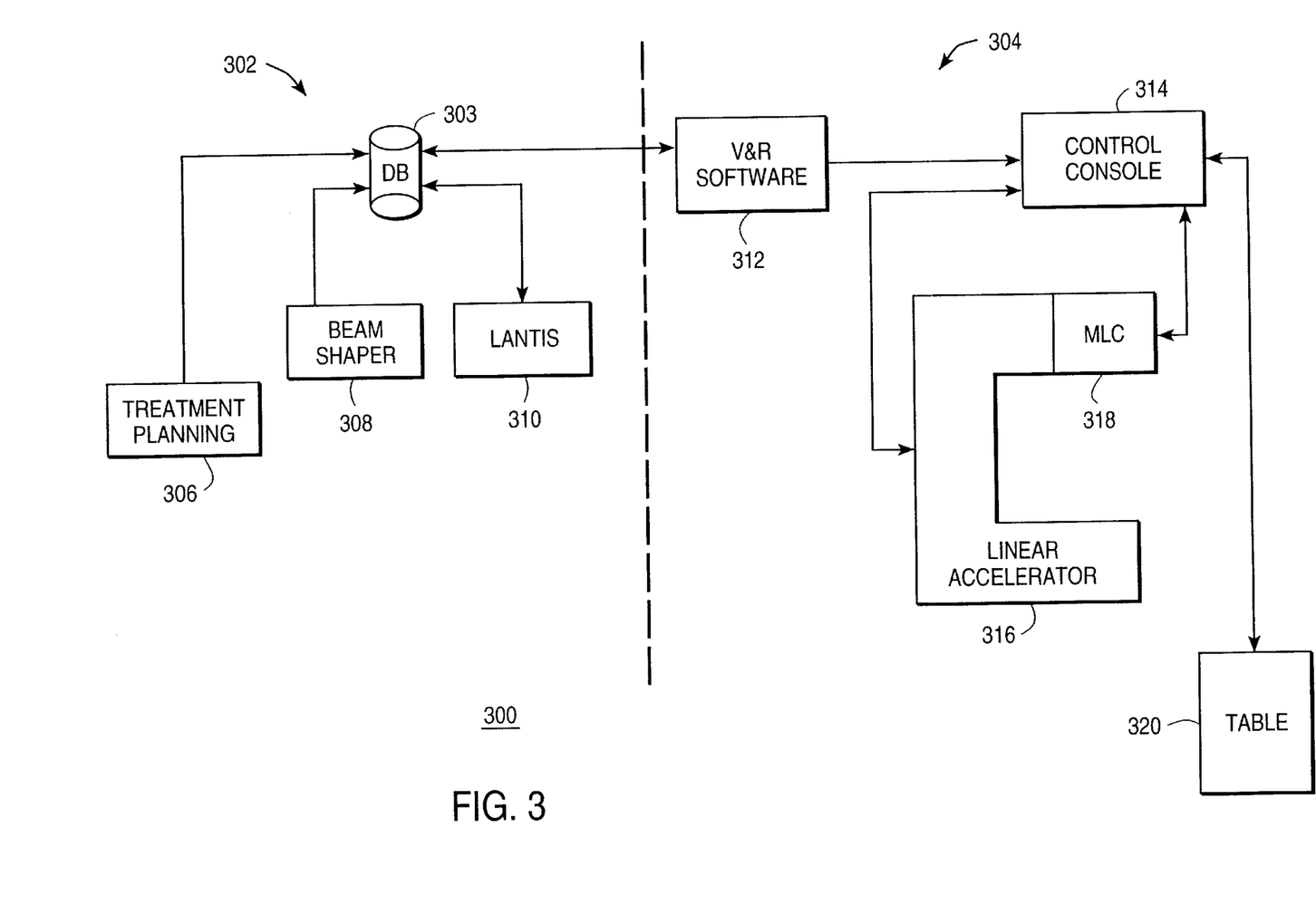
FIG. 3 illustrates a block diagram of a system for treating a patient.

To address the problems associated with lead alloy block and conventional MLC systems, a high definition intensity MLC system is provided which allows for increased dosages with improved conformal radiation therapy. In addition, a system and method in accordance with the present invention provides for minimal leakage. FIG. 3 illustrates a block diagram of a system 300 for treating a patient. The system 300 is divided into two phases, a planning phase 302 and a treatment phase 304.

The planning phase 302 comprises a database 303 which receives treatment fields from treatment planning system 306, beam shaper 308 and local area therapy information system (LANTIS) 310. The treatment planning system 306 is typically a very sophisticated system used by a doctor or the like to provide certain information about a particular manner of treating a tumor or the like. One of the functions of the treatment planning system 306 would be to provide a translation of the table as well as the information to the positioning of the leafs on the multileaf collimator.

The beam shaper 308 and the LANTIS 310 similarly provide field information to the database 303 to provide the information related to table position and leaf position information. Verification and Recording (V&R) software 312 and LANTIS 310 are utilized to provide segments to, and receive information, from the database 303 related to the control of the multileaf collimator 318 as well as the positioning of the table 320 along with the control of the linear accelerator of the treatment system 316. A typical V&R software package is for example PRIMEVIEW, a software package sold by Siemens Corporation. The V&R software 312 in the treatment phase 304 receives and provides the information to control console 314. The control console in turn controls the linear accelerator 316, the MLC 318 and the table 320. Accordingly, the present invention could be located in the planning phase or the treatment phase as well as in the treatment system to provide the appropriate radiation therapy. Specifically, a high definition intensity MLC system could be provided in the V&R software, such as PRIMEVIEW, to provide the appropriate radiation therapy.

Figure 4:
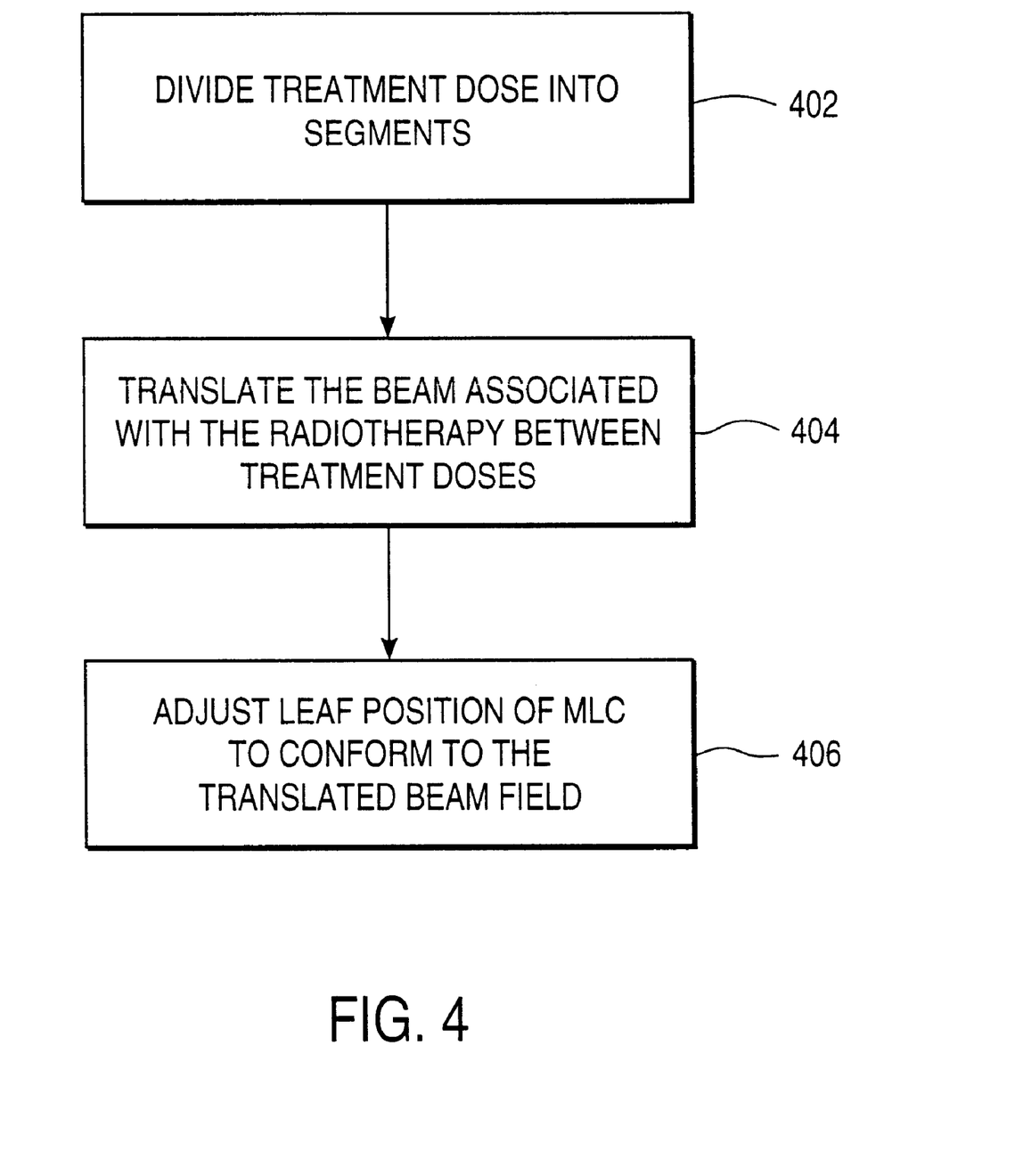
FIG. 4 if a flow chart of a HDI MLC system in accordance with the present invention in this embodiment.

To describe the operation of the present invention in more detail, refer now to FIG. 4.

High Definition Intensity (HDI) MLC System

FIG. 4 is a flow chart of a HDI MLC system in accordance with the present invention in this embodiment. First, the treatment port dose is divided into segments, via step 402. Next, the beam associated with the radiotherapy is translated between doses, via step 404. In a preferred embodiment the beam is translated a subincrement of the leaf width perpendicular to the leaf motion axis. Another possibility is to rotate the MLC in varying degrees. Finally, the leaf positions of the MLC are adjusted to maintain the shape, via step 406.

In one embodiment, if a port is treated with a standard 1 cm width MLC leaf and the field was divided into two, then each of the two fields would be treated with half of the dose. Between fields one and two a translation by 5 mm of the field perpendicular to the leaf motion axis would occur and the leaf positions would be altered to maintain the correct port shape. Producing a conformal field by this manner produces a 5 mm resolution of the beam edge and reduces the original leakage by one half.

The HDI MLC system allows for a much more conformal shape than the original 1 cm MLC leaf widths. This translation of the field and the repositioning of the leaves can be accomplished through an automated control and the treatment overhead would be minimal as compared to a standard block shaped treatment.

Figure 5:
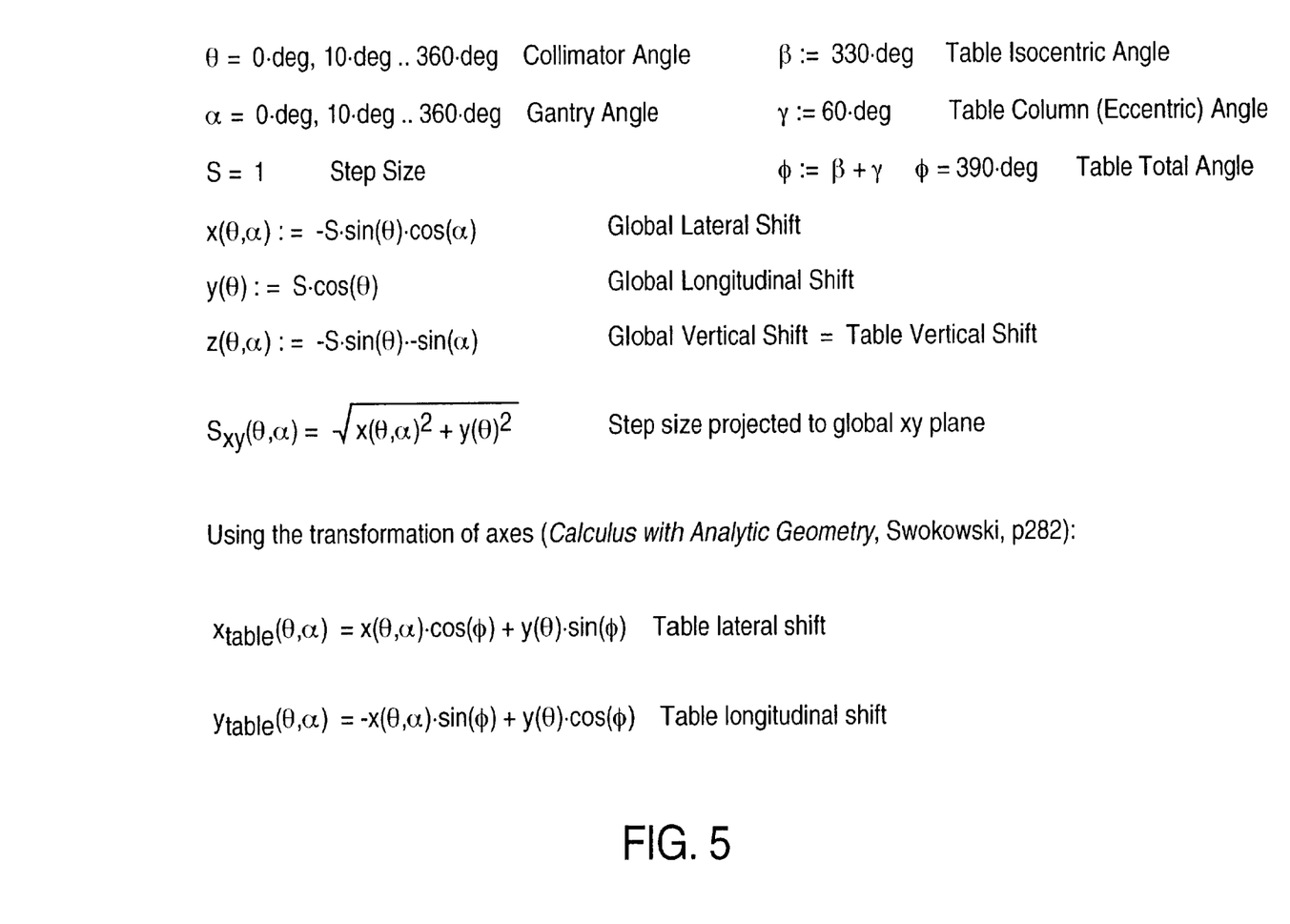
FIG. 5 illustrates the parameters and tables that could be used to determine the incremental table movement when utilizing a system and method in accordance with the present invention.

It is important when using the HDI to move the table in a precise fashion in three dimensions to insure that the multiple doses are administered accurately. FIG. 5 illustrates the parameters and tables that could be used to determine the incremental table movement when utilizing a system and method in accordance with the present invention.

Interleaf leakage is a problem with conventional multileaf collimator systems as the dosage amount increases. Each time another field division occurs the amount of interleaf leakage drops by one half. For example, a 5 mm shift has interleaf leakage of approximately 0.7% and for a 3 mm shift a leakage of approximately 0.3%. When implementing this clinically, a geometric algorithm is needed to calculate the amount of translation in any of the three planes (x, y, and z vector), as well as the leaf movements that are required.

A system and method in accordance with the present invention is particularly useful for clinical application delivering a much more conformal field at a significant reduction in x-ray leakage to that of a custom block and a MLC leaf design of smaller leaf width.

The following will discuss in more detail a preferred embodiment of the present invention.

HDI Overview

A HDI method and system, in a preferred embodiment, will be integrated with automatic table motion and MLC support. HDI functionality will allow the user to select an MLC field to be converted to a HDI field. During the conversion, the user will be able to select the desired resolution of the HDI field. A HDI field is a group of fields that are to be auto-sequenced together to create the HDI field definition.

HDI functionality can exist completely within the planning phase or the treatment phase. This will allow the new functionality to take advantage of existing interfaces to the database for creating fields and autosequenced groups. HDI functionality is an automated method of creating new fields with new MLC shapes, new table parameters, and new grouping arrangements, which are all done manually today.

In a preferred embodiment, the core functionality of HDI will be contained within a HDI dialog for visualizing target shape and HDI definition.

These functional requirements include:

The ability to create HDI fields and groups from one MLC field. Each field will have new field shapes and new table parameters.

The ability to select the resolution for the HDI fields.

The ability to visualize the results of the HDI fields and resolution sections.

A new auto-sequence group type for HDI fields with special group rules.

The ability to deliver, verify and record the HDI group and fields.

The ability to port a HDI group

Functional Requirements

Figure 6:
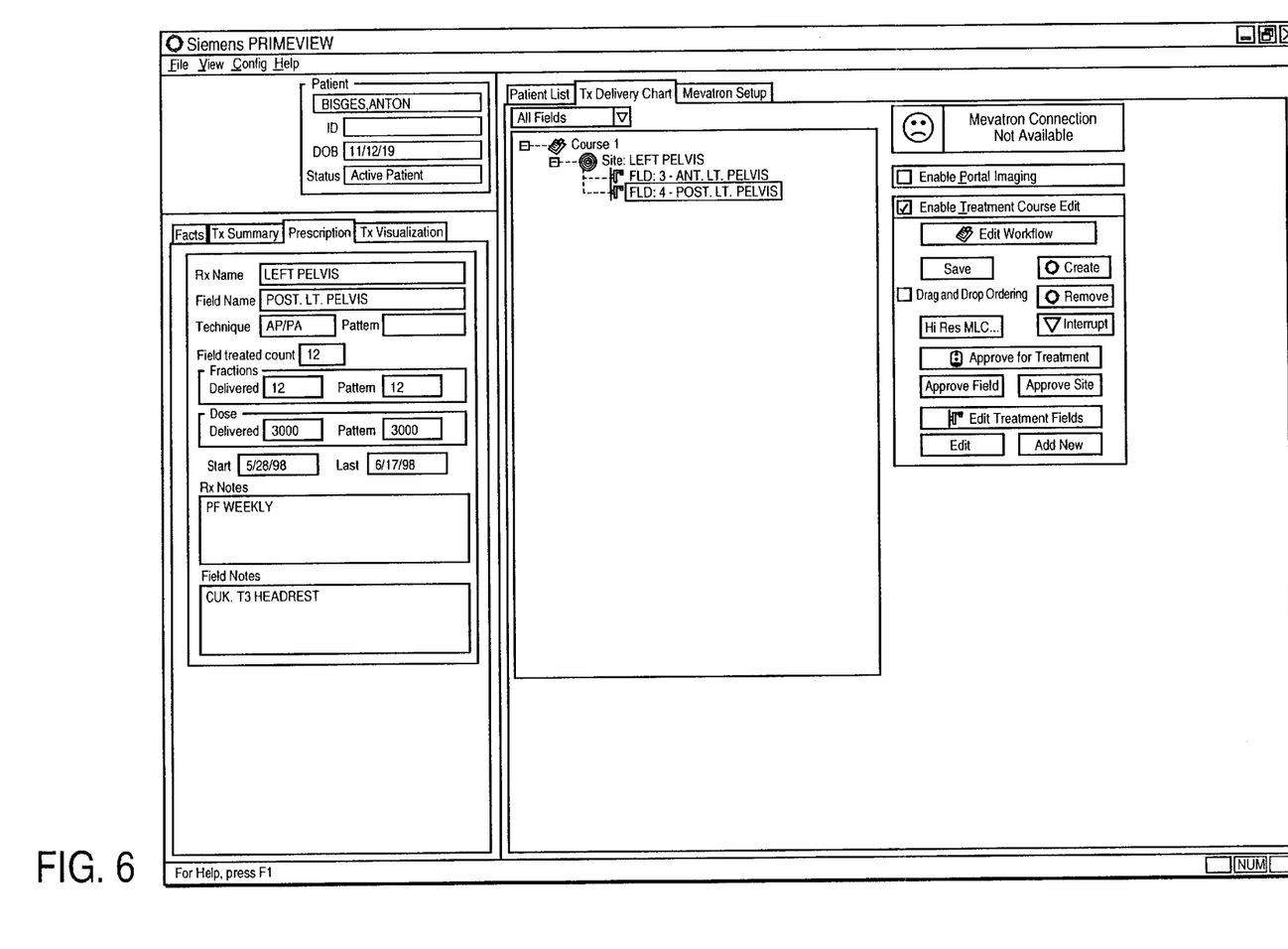
FIG. 6 illustrates a Dialog in which a portion of the pelvis is to be treated.

An HDI dialog illustrates the MLC shape dependent upon the fields generated. This information is then provided to the control console which in turn controls the position of the leafs of the MLC. FIG. 6 illustrates a Dialog in which a portion of the pelvis is to be treated. The preferred embodiment of the operation of the HDI Dialog is described below.

B. HDI Dialog

1. The HDI dialog will provide a HDI display of the MLC shape and a projection of the logical MLC leaf edges.
2. The HDI dialog will provide a control for setting the desired resolution of the logical leaf boundaries.
3. The HDI display will be dynamically controlled by the resolution control.
4. The HDI display comprises a grayscale image showing the overlapping HDI field shapes. This will be similar to the TxVisualization tab display.
5. The HDI display will take into account the derived table positions for each HDI field when displaying the overlapping fields.
6. The HDI dialog will provide a save button and a cancel button.
7. When the user selects save, the HDI dialog will create new fields corresponding to the original field and the selected resolution.
8. The resolution control shall provide options, for example:
   None
   5.0 mm
   3.3 mm
   2.5 mm
   2.0 mm
9. The save button shall be disabled when none is selected on the resolution control.
10. Based on a defined algorithm, one new field shall be created when the save button is clicked and 5.0 mm is selected on the resolution control.
11. Based on a defined algorithm, 2 new fields shall be created when the save button is clicked and 3.3 mm is selected on the resolution control.
12. Based on a defined algorithm, 3 new fields shall be created when the save button is clicked and 2.5 mm is selected on the resolution control.
13. Based on a defined algorithm, 4 new fields shall be created when the save button is clicked and 2.0 mm is selected on the resolution control.

Figure 7:
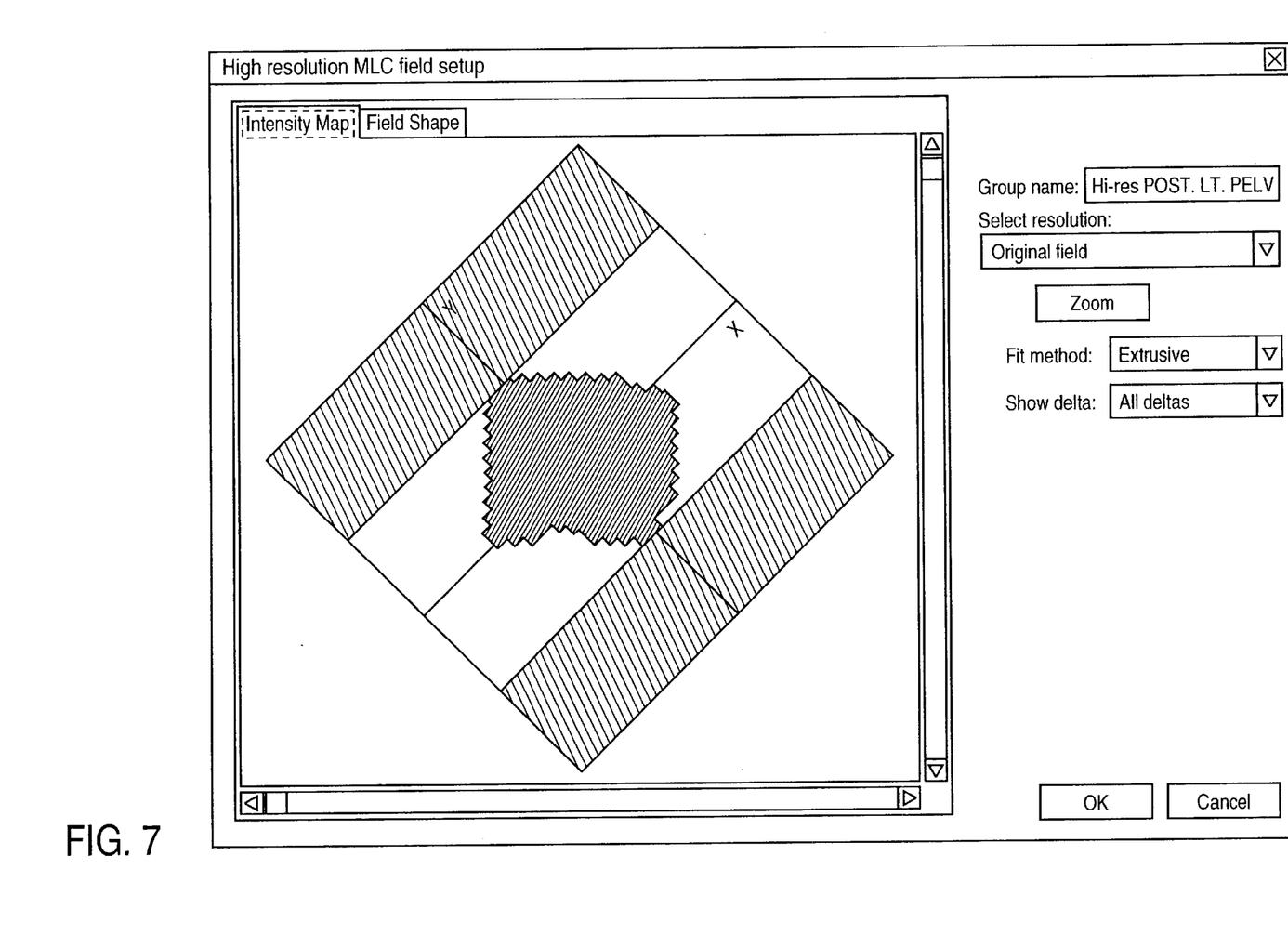
FIG. 7 illustrates a Dialog with field being created around a body i.e., tumor).
Figure 8:
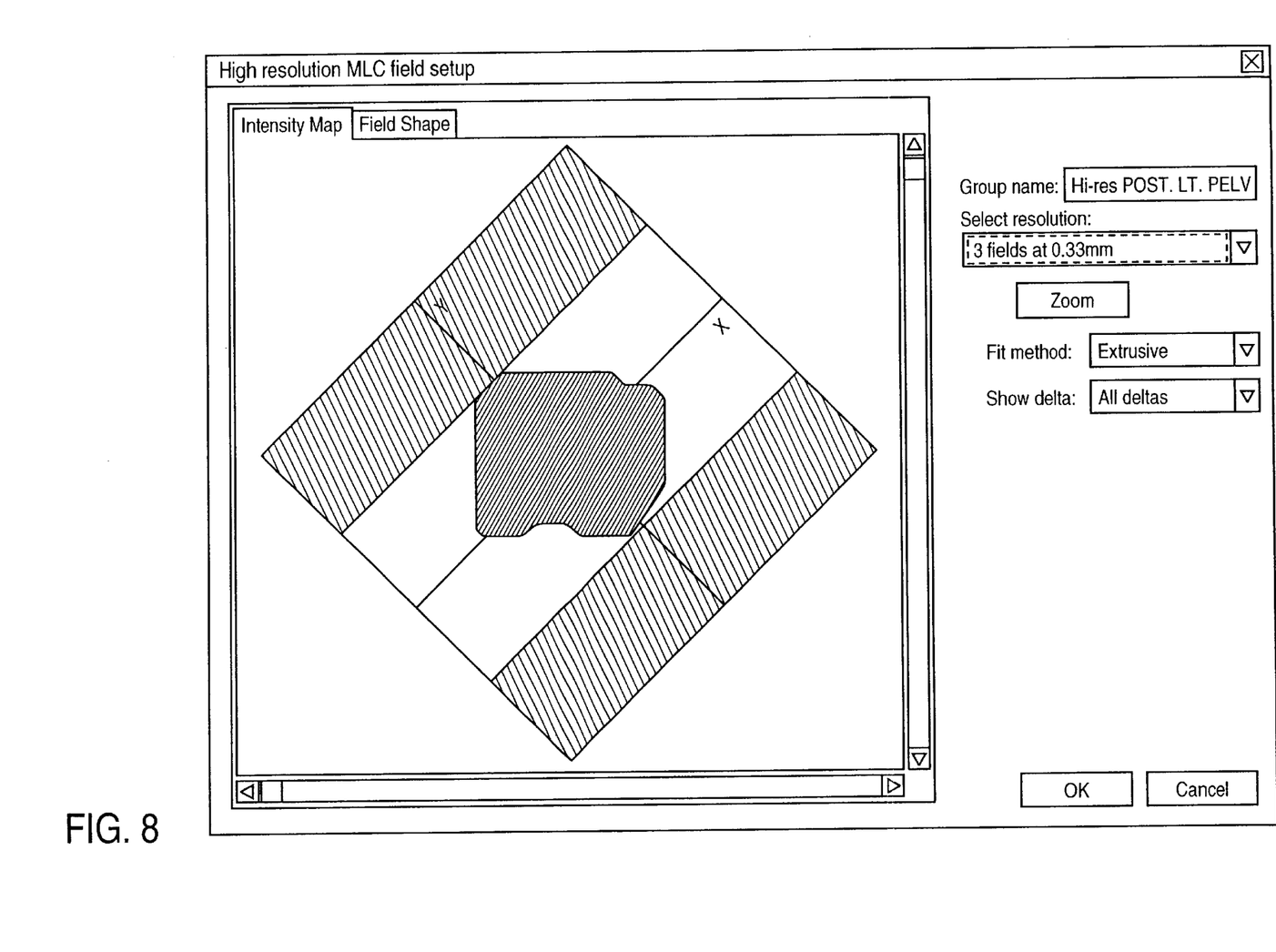
FIG. 8 illustrates a second dialog with three new fields being created.

FIG. 7 illustrates a first dialog with field being created around a body (i.e., tumor). Note the stairstep effect created by the field. FIG. 8 illustrates a second dialog with three new fields being created. As shown, the three new fields match the contour of the body image more conformally.

Accordingly, a system and method in accordance with the present invention provides for better defined edges around target and critical surfaces than a conventional multileaf collimator (i.e., effective penumbra). It provides for the same clearance as conventional MLC. It provides for the same maximum field size as a conventional MLC. Finally, a system and method in accordance with the present invention minimizes leakage between the leafs thereby minimizing leakage to the patient.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the present invention.

What is claimed is:

1. A method for providing conformal radiation therapy of an object utilizing a multileaf collimator, comprising the steps of:
   (a) prescribing a total dose to be applied to the object;
   (b) dividing the total dose into a number of subdoses;
   (c) defining a plurality of treatment fields corresponding to the object, the plurality of treatment fields depending on the number of subdoses;
   (d) locating one of the treatment fields of the plurality of treatment fields;
   (e) adjusting the multileaf collimator along a longitudinal axis to define a shape of the one treatment field;
   (f) irradiating the one treatment field with one of the number of subdoses, the irradiating step further comprising the steps of:
      (f1) delivering a portion of one of the number of subdoses to the one treatment field;
      (f2) translating a beam associated with the radiation therapy;
      (f3) adjusting the multileaf collimator to maintain the shape of the one treatment field; and
      (f4) delivering another portion of the one subdose; and
      (f5) repeating steps (f2)–(f4) until all of the one subdose has been delivered, whereby a stair step effect at the edge of the one treatment field is minimized; and
   (g) repeating steps (d)–(f) until each of the plurality of treatment fields has been irradiated.

2. The method of claim 1 wherein the one subdose comprises two portions.

3. The method of claim 1 wherein the one subdose comprises three portions.

4. The method of claim 1 wherein the translating and adjusting steps are provided through an automated control.

5. The method of claim 4 wherein the translating step (f2) comprises translating a predetermined distance of the field associated with the number of portions.

6. The method of claim 5 wherein the adjusting step comprises repositioning the leaves of the multileaf collimator.

7. The method of claim 6 wherein a geometric algorithm is utilized to calculate the amount of translation and the repositioning of the leaves.

8. The method of claim 4, wherein the translating step comprises rotating the MLC in varying degrees.

9. A computer readable medium containing programming instructions for providing conformal radiation therapy of an object utilizing a multileaf collimator, the programming instructions for:
   (a) prescribing a total dose to be applied to the object;
   (b) dividing the total dose into a number of subdoses;
   (c) defining a plurality of treatment fields corresponding to the object, the plurality of treatment fields depending on the number of subdoses;
   (d) locating one of the treatment fields of the plurality of treatment fields; adjusting the multileaf collimator along a longitudinal axis to define a shape of the one treatment field;
   (f) irradiating the one treatment field with one of the number of subdoses, the irradiating instruction further comprising the instructions for:
      (f1) delivering a portion of one of the number of subdoses to the one treatment field;
      (f2) translating a beam associated with the radiation therapy;
      (f3) adjusting the multileaf collimator to maintain the shape of the one treatment field; and
      (f4) delivering another portion of the one subdose; and
      (f5) repeating steps (f2)–(f4) until the subdose has been delivered, whereby a stair step effect at the edge of the one treatment field is minimized; and
   (g) repeating steps (d)–(f) until each of the plurality of treatment fields has been irradiated.

10. The computer readable medium of claim 9 wherein the one subdose comprises two portions.

11. The computer readable medium of claim 9 wherein the subdose comprises three portions.

12. The computer readable medium of claim 9, wherein the translating and adjusting instructions are provided through an automated control.

13. The computer readable medium of claim 12, wherein the translating instruction (f2) comprises translating a predetermined distance of the field associated with the number of portions.

14. The computer readable medium of claim 13 wherein the adjusting instruction comprises repositioning the leaves of the multileaf collimator.

15. The computer readable medium of claim 14 wherein a geometric algorithm is utilized to calculate the amount of translation and the repositioning of the leaves.

* * * * *